US012622966B2

(12) United States Patent
Lee et al.

(10) Patent No.: US 12,622,966 B2
(45) Date of Patent: May 12, 2026

(54) COMPOUND FOR PHOTOTHERMAL CANCER THERAPY, COMPOSITION INCLUDING THE SAME, AND METHOD FOR PHOTOTHERMAL CANCER THERAPY

(71) Applicant: PUKYONG NATIONAL UNIVERSITY INDUSTRY-UNIVERSITY COOPERATION FOUNDATION, Busan (KR)

(72) Inventors: Song Yi Lee, Busan (KR); Thanh Chung Pham, Busan (KR)

(73) Assignee: PUKYONG NATIONAL INDUSTRY-UNIVERSITY COOPERATION FOUNDATION, Busan (KR)

( * ) Notice: Subject to any disclaimer, the term of this patent is extended or adjusted under 35 U.S.C. 154(b) by 530 days.

(21) Appl. No.: 18/162,658

(22) Filed: Jan. 31, 2023

(65) Prior Publication Data

US 2023/0338538 A1 Oct. 26, 2023

(30) Foreign Application Priority Data

Apr. 19, 2022 (KR) ........................ 10-2022-0048172

(51) Int. Cl.

| | |
|---|---|
| ***A61K 41/00*** | (2020.01) |
| ***A61B 18/00*** | (2006.01) |
| ***A61B 18/20*** | (2006.01) |
| ***A61K 9/00*** | (2006.01) |
| ***A61K 9/14*** | (2006.01) |
| ***A61K 9/51*** | (2006.01) |
| ***A61N 5/06*** | (2006.01) |
| ***A61N 5/067*** | (2006.01) |
| ***A61P 35/00*** | (2006.01) |
| ***C07C 255/30*** | (2006.01) |
| ***C07C 255/31*** | (2006.01) |
| ***C07C 255/61*** | (2006.01) |

(52) U.S. Cl.

CPC ............ *A61K 41/0052* (2013.01); *A61K 9/51* (2013.01); *A61P 35/00* (2018.01); *C07C 255/61* (2013.01); *A61N 5/062* (2013.01); *A61N 5/0625* (2013.01); *A61N 2005/0663* (2013.01); *A61N 5/067* (2021.08); *C07C 2602/08* (2017.05)

(58) Field of Classification Search

CPC . C07C 255/61; C07C 2602/08; C07C 255/31; C07C 255/30

See application file for complete search history.

(56) References Cited

U.S. PATENT DOCUMENTS

| | | | | |
|---|---|---|---|---|
| 5,028,708 A * | 7/1991 | Hioki | .................... | C07C 255/00 546/171 |
| 5,220,027 A * | 6/1993 | Hioki | .................... | C07C 255/00 546/171 |
| 6,120,983 A | 9/2000 | Okada et al. | | |

FOREIGN PATENT DOCUMENTS

| | | |
|---|---|---|
| EP | 0287377 B1 | 9/1993 |

OTHER PUBLICATIONS

Ni, Jen-Shyang , et al., "Photoinduced Nonadiabatic Decay-guided Molecular Motor Triggers Effective Photothermal Conversion for Hyperthermia Cancer Therapy", Angew. Chem Int. Ed., 59,, 2020, 11298-11302.

Tan, Yonghong , et al., "NIR-II Aggregation-Induced Emission Luminogens for Tumor Phototheranostics", Biosensors, 12,, Jan. 17, 2022.

* cited by examiner

*Primary Examiner* — Bruck Kifle
*Assistant Examiner* — Kevin S Martin
(74) *Attorney, Agent, or Firm* — HOLZER PATEL DRENNAN

(57) ABSTRACT

Provided are a new compound for photothermal cancer therapy, a composition including the same, and a method for photothermal cancer therapy, and more particularly, a compound that is an organic photosensitizer based on an indan structure, a nanoparticle as a self-assembly thereof, a composition including the same, and a method for photothermal therapy using the same.

11 Claims, 6 Drawing Sheets

NI2

NI2 NPs

COMPOUND FOR PHOTOTHERMAL CANCER THERAPY, COMPOSITION INCLUDING THE SAME, AND METHOD FOR PHOTOTHERMAL CANCER THERAPY

CROSS-REFERENCE TO RELATED APPLICATION

This application claims the benefit of Korean Patent Application No. 10-2022-0048172 filed on Apr. 19, 2022, in the Korean Intellectual Property Office, the entire disclosure of which is incorporated herein by reference for all purposes.

BACKGROUND

1. Field of the Invention

One or more embodiments relate to a new compound for photothermal cancer therapy, a composition including the same, and a method for photothermal cancer therapy.

2. Description of the Related Art

Chemotherapy, radiation therapy, and surgery, which have been applied to cancer treatment so far, often cause serious side effects. In contrast, photothermal therapy has advantages such as low side effects, very low drug resistance, local destruction of tumor, and the like. Photothermal therapeutic agents are mostly based on inorganic materials, but organic photothermal agents have better biocompatibility. Among organic photothermal agents, polymers generally exhibit molecular polydispersity with low reproducibility, and supramolecules are not always stable under physiological conditions, and the polymers and the supramolecules have disadvantages of biodegradation toxicity.

Several efficient small organic photothermal agents have been reported, but in order to make these organic photothermal agents having a photothermal effect, a bulky chain, an aromatic ring, etc. are introduced to perform several stages of organic reaction, resulting in a low yield, so that economic disadvantages also occur in commercialization, clinical trials and applications. Some small organic photothermal agents have problems such as low photostability of cyanide derivatives, low water solubility of porphyrins and phthalocyanines, and low photothermal conversion efficiency of BODIPY derivatives, and a molecular design for nanoscale-level organic photothermal agents for acquiring excellent photothermal conversion efficiency (η) may generate obstacles to rapidly access biological and clinical trials.

SUMMARY

An aspect of the present disclosure is to provide a new compound that is a photosensitizer having a simple synthesis process (e.g., a single-step organic reaction), excellent photothermal conversion efficiency and excellent biocompatibility and may be used as a photothermal material.

Another aspect of the present disclosure is to provide nanoparticles that are a nano-aggregation platform prepared by self-assembly of the compound according to the present disclosure, and may be utilized as a photothermal material having excellent photothermal conversion efficiency and excellent biocompatibility.

Another aspect of the present disclosure is to provide a composition that includes the compound, nanoparticles or both according to the present disclosure and may be utilized as a photothermal therapeutic agent.

Another aspect of the present disclosure is to provide a photothermal therapy method using the composition according to the present disclosure.

However, technical aspects of the present disclosure are not limited to the aforementioned purpose and other aspects which are not mentioned may be clearly understood to those skilled in the art from the following description.

According to an aspect of the present disclosure, there is provided a new compound represented by Chemical Formula 1 below:

[Chemical Formula 1]

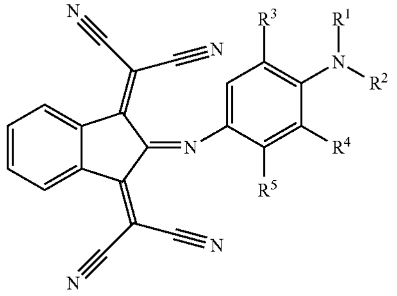

In Chemical Formula 1, $R^1$ and $R^2$ are selected from hydrogen, a substituted or unsubstituted cycloalkyl group having 3 to 20 carbon atoms, a substituted or unsubstituted cycloalkenyl group having 3 to 20 carbon atoms, a substituted or unsubstituted aryl group having 6 to 30 carbon atoms, a substituted or unsubstituted heteroaryl group having 5 to 30 carbon atoms, an alkyl group having 1 to 20 carbon atoms, an alkenyl group having 2 to 20 carbon atoms, and an alkynyl group having 2 to 20 carbon atoms, respectively, however, at least one of $R^1$ and $R^2$ is selected from a substituted or unsubstituted cycloalkyl group having 3 to 20 carbon atoms, a substituted or unsubstituted cycloalkenyl group having 3 to 20 carbon atoms, a substituted or unsubstituted aryl group having 6 to 30 carbon atoms, and a substituted or unsubstituted heteroaryl group having 5 to 30 carbon atoms.

$R^3$ to $R^5$ are selected from hydrogen, halogen, a hydroxyl group, an alkyl group having 1 to 10 carbon atoms, an alkenyl group having 2 to 10 carbon atoms, and an alkynyl group having 2 to 10 carbon atoms, respectively.) According to an embodiment of the present disclosure, at least one of the $R^1$ and $R^2$ may be selected from a substituted or unsubstituted aryl group having 6 to 12 carbon atoms and a substituted or unsubstituted heteroaryl group having 5 carbon atoms.

According to an embodiment of the present disclosure, the compound of Chemical Formula 1 may be selected from Chemical Formula 1-1.

[Chemical Formula 1-1]

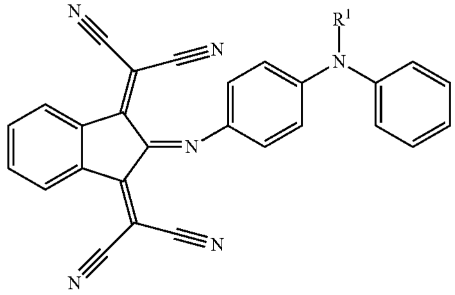

In Chemical Formula 1-1, $R^1$ is selected from hydrogen, a substituted or unsubstituted cycloalkyl group having 3 to 6 carbon atoms, a substituted or unsubstituted cycloalkenyl group having 3 to 6 carbon atoms, a substituted or unsubstituted aryl group having 6 to 12 carbon atoms, a substituted or unsubstituted heteroaryl group having 5 to 12 carbon atoms, an alkyl group having 1 to 10 carbon atoms, an alkenyl group having 2 to 10 carbon atoms, and an alkynyl group having 2 to 10 carbon atoms.

According to an embodiment of the present disclosure, the compound may be an organic photosensitizer, and the compound may be an organic photosensitizer for photothermal therapy.

According to another aspect of the present disclosure, there is provided a nanoparticle including the compound represented by Chemical Formula 1 above. The nanoparticle may be a nanoparticle in which the compound of Chemical Formula 1 is self-assembled in an aqueous solvent.

According to an embodiment of the present disclosure, the nanoparticle may have a size of 500 nm or less, and the nanoparticle may emit heat at a temperature of 45° C. or higher by a light irradiation.

According to an embodiment of the present disclosure, the nanoparticle may include an organic photosensitizer, and the nanoparticle may include an organic photosensitizer for photothermal therapy.

According to an embodiment of the present disclosure, the photothermal conversion efficiency of the nanoparticle may be 60% or higher.

According to another aspect of the present disclosure, there is provided a composition including the compound represented by Chemical Formula 1 according to the present disclosure, the nanoparticle according to the present disclosure, or both.

According to an embodiment of the present disclosure, the composition may be used for photothermal therapy, and emit thermal energy during a light irradiation to remove or kill target cells.

According to an embodiment of the present disclosure, the target cells may be cancer cells, tumor cells or hyperproliferative cells.

According to an embodiment of the present disclosure, the composition may further include water, an organic solvent, or both, in which the compound, the nanoparticle or both in the composition may be included in an active ingredient content.

According to another aspect of the present disclosure, there is provided a method for photothermal therapy including contacting the composition of the present disclosure with a target cell in vivo or ex vivo, and irradiating light to a region of the target cell contacting the composition.

According to an embodiment of the present disclosure, the irradiating of the light may include heating a target cell region to a temperature of 45° C. or more by irradiating a red light laser of 1 second or more and 1 $W/cm^2$ or more and removing or killing the target cell.

According to an embodiment of the present disclosure, the method may further include, after the irradiating of the light, acquiring and analyzing an infrared thermal image of the target cell region.

BRIEF DESCRIPTION OF THE DRAWINGS

These and/or other aspects, features, and advantages of the invention will become apparent and more readily appreciated from the following description of embodiments, taken in conjunction with the accompanying drawings of which:

FIG. 3A illustrates temperature rise measured in NI2 NPs at various concentrations (0 for distilled water, 25, 50, 75, and 100 μM) after irradiation for 150 seconds (N=4); FIG. 3B illustrates photothermal convergence efficiency (PCE) of NI2 NPs (100 μM) in 4 ON/OFF cycles of laser irradiation (ON/OFF time=150 s/450 s; duty cycle=25%); and FIG. 3C illustrates infrared thermal images of NI2 NPs (100 μM) captured at various irradiation times (scale bar=5 mm);

FIG. 4A illustrates cell viability of CT26 cells cultured for 24 hours in NI2 NPs (0, 25, 50, 75 and 100 μM); FIG. 4B illustrates cell viability of CT26 cells treated with "laser" (1.5 W/cm2), "NI2 NPs" (100 μM) and "laser+NI2 NPs" (laser at 1.5 $W/cm^2$+100 μM of NI2 NPs); and FIG. 4C illustrates fluorescent images of treated cells after FDA/PI staining (Fluorescein Diacetate/Propidium Iodide staining). Live cells and dead cells were stained with FDA (green) and PI (red, scale bar=200 μm), respectively. The relative fluorescence intensities of green in FIG. 4D and red in FIG. 4E were compared for the various treatment groups (N=4 per group, **MU $p<0.005$ vs. CTRL);

FIG. 5A illustrates a temporal change in temperature during treatment and FIG. 5B illustrates relevant thermal images captured at various heat treatment times (N=4 per group; CTRL=control; TM=tumor region; scale bar=10 mm). In particular, a white arrow in FIG. 5B indicates a laser irradiation direction; FIG. 6A shows plan view images captured at various time points after treatment (TM=tumor region; D=day; scale bar=10 mm), FIG. 6B shows changes in body weight of treated animals, FIG. 6C shows changes in volume of treated tumors, and FIG. 6D shows HE-straining images of tumors acquired in various treated groups in D10 (top row=100× and scale bar=100 μm; bottom row=400× and scale bar=30 μm). In particular, arrows in FIG. 6D indicate the positions of blood capillaries. Solid boxes in the top images are magnified in the bottom images (N=4 per group; **MU $p<0.005$ vs. CTRL).

DETAILED DESCRIPTION

Figure 1A:
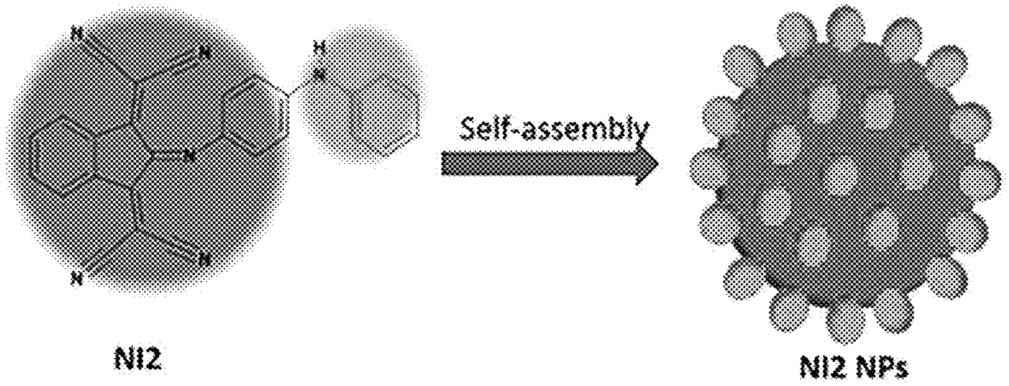
FIG. 1A illustrates a schematic diagram of a preparing process of a nanoparticle (e.g., NI2 NP) by a self-assembly process of a compound of the present disclosure

Hereinafter, embodiments of the present disclosure will be described in detail. In describing the embodiment of the present disclosure, a detailed description of known functions or constitutions will be omitted if it is determined that they unnecessarily make the gist of the present disclosure unclear. Terminologies used herein are a terminologies used to properly express embodiments of the present disclosure, which may vary according to a user, an operator's intention, or customs in the art to which the present disclosure pertains. Accordingly, definitions of the terminologies need to be described based on contents throughout this specification.

Throughout this specification, it will be understood that when a member is referred to as being "on" another member, it may be directly on the other member or intervening members may also be present.

Throughout the specification, when a certain part "comprises" a certain component, it will be understood to imply the inclusion of stated elements but not the exclusion of any other elements.

The present disclosure relates to a new organic photosensitizer compound, and according to an embodiment of the present disclosure, the compound may be an organic photosensitizer compound based on an indan structure represented by Chemical Formula 1 below.

[Chemical Formula 1]

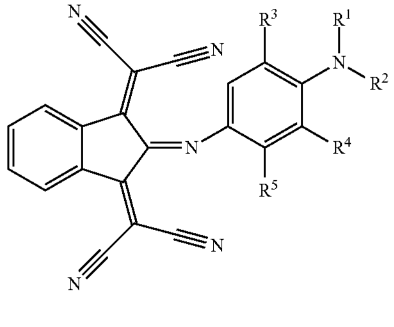

As an example of the present disclosure, in Chemical Formula 1, $R^1$ and $R^2$ may be selected from hydrogen, a substituted or unsubstituted cycloalkyl group having 3 to 20 carbon atoms, a substituted or unsubstituted cycloalkenyl group having 3 to 20 carbon atoms, a substituted or unsubstituted aryl group having 6 to 30 carbon atoms, a substituted or unsubstituted heteroaryl group having 5 to 30 carbon atoms, an alkyl group having 1 to 20 carbon atoms, an alkenyl group having 2 to 20 carbon atoms, and an alkynyl group having 2 to 20 carbon atoms, respectively.

As an example of the present disclosure, at least one of $R^1$ and $R^2$ may be a ring group selected from a substituted or unsubstituted cycloalkyl group having 3 to 20 carbon atoms, a substituted or unsubstituted cycloalkenyl group having 3 to 20 carbon atoms, a substituted or unsubstituted aryl group having 6 to 30 carbon atoms, and a substituted or unsubstituted heteroaryl group having 5 to 30 carbon atoms. In any example, one of $R^1$ and $R^2$ may be selected from a substituted or unsubstituted aryl group having 6 to 30 carbon atoms and a substituted or unsubstituted heteroaryl group having 5 to 30 carbon atoms, and the other thereof may be selected from hydrogen, an alkyl group having 1 to 20 carbon atoms, an alkenyl group having 2 to 20 carbon atoms and an alkynyl group having 2 to 20 carbon atoms. In any example, at least one of $R^1$ and $R^2$ may be selected from a substituted or unsubstituted aryl group having 6 to 14 carbon atoms.

As an example of the present disclosure, $R^3$ to $R^5$ may be selected from hydrogen, halogen, a hydroxyl group, an alkyl group having 1 to 10 carbon atoms, an alkenyl group having 2 to 10 carbon atoms, and an alkynyl group having 2 to 10 carbon atoms, respectively. In any example, $R^3$ to $R^5$ may be selected from hydrogen and halogen, respectively. In any example, $R^3$ to $R^5$ may be hydrogen.

As an example of the present disclosure, the compound of Chemical Formula 1 may be selected from Chemical Formula 1-1.

[Chemical Formula 1-1]

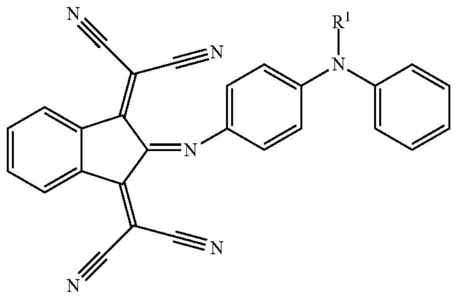

As an example of the present disclosure, in Chemical Formula 1-1, $R^1$ may be selected from hydrogen, a substituted or unsubstituted cycloalkyl group having 3 to 6 carbon atoms, a substituted or unsubstituted cycloalkenyl group having 3 to 6 carbon atoms, a substituted or unsubstituted aryl group having 6 to 14 carbon atoms, a substituted or unsubstituted heteroaryl group having 5 to 14 carbon atoms, an alkyl group having 1 to 10 carbon atoms, an alkenyl group having 2 to 10 carbon atoms, and an alkynyl group having 2 to 10 carbon atoms, respectively.

As an example of the present disclosure, for example, the alkyl may be alkyl having 1 to 20 carbon atoms; 1 to 10 carbon atoms; or 1 to 5 carbon atoms, and may be a straight chain or branched chain.

For example, the alkenyl may be alkenyl having 2 to 20 carbon atoms; 2 to 10 carbon atoms; or 2 to 5 carbon atoms, and may be a straight chain or branched chain.

For example, the alkynyl may be alkynyl having 2 to 20 carbon atoms; 2 to 10 carbon atoms; or 2 to 5 carbon atoms, and may be a straight chain or branched chain.

For example, the cycloalkyl may be cycloalkyl having 3 to 20 carbon atoms; 4 to 20 carbon atoms; or 5 to 8 carbon atoms, and may be substituted or unsubstituted.

For example, the cycloalkenyl may be cycloalkenyl having 3 to 20 carbon atoms; 4 to 20 carbon atoms; or 5 to 8 carbon atoms, and may be substituted or unsubstituted.

For example, the aryl may be aryl having 6 to 30 carbon atoms; 6 to 20 carbon atoms; 6 to 14 carbon atoms; 6 to 12 carbon atoms; or 6 to 10 carbon atoms. For example, the aryl may be a fused aromatic ring or biaryl. For example, the aryl may be phenyl, tolyl, xylene, biphenolyl, naphthyl, anthryl, phenanthryl, and the like.

For example, the heteroaryl may be heteroaryl having 5 to 30 carbon atoms; 5 to 20 carbon atoms; 5 to 14 carbon atoms; or 5 to 10 carbon atoms.

For example, the heteroaryl includes at least 1 to 3 heteroatoms in each ring, and the heteroatoms may be at least one selected from nitrogen (N), oxygen (O), and sulfur (S) heteroatoms.

For example, the halogen may be selected from —F, —Br, —Cl and —I.

For example, the substitution may be performed with alkyl having 1 to 5 carbon atoms, alkenyl having 2 to 5 carbon atoms, alkynyl having 2 to 5 carbon atoms, a halogen atom, and the like.

Figure 1B:
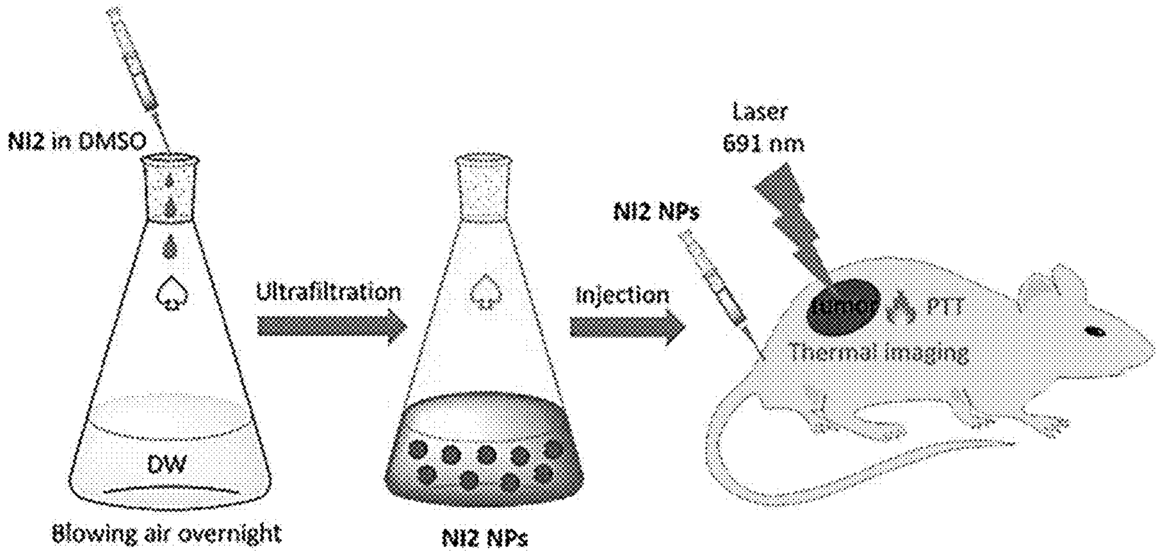
FIG. 1B illustrates a preparing process of nanoparticles (e.g., NI2 NPs) by a self-assembly process in a solvent and a photothermal therapy process of nanoparticles (e.g. NI2 NPs) in a tumor in vivo, according to an embodiment of the present disclosure.

According to an embodiment of the present disclosure, the compound is an organic photosensitizer, and the compound may be applied as an organic photosensitizer (e.g., organic photothermal agent) for photothermal therapy. That is, the compound represented by Chemical Formula 1 may be synthesized by a single organic reaction with the compound having the indan basic structure, as illustrated in FIG. 1. The compound may be further prepared into nano-aggregates by a simple process such as self-assembly in a solvent. This may provide a photothermal therapy material having high photothermal conversion efficiency, high biocompatibility, and economic feasibility of a synthesis process.

The present disclosure relates to a nanoparticle including an organic photosensitizer according to the present disclosure, and according to an embodiment of the present disclosure, the organic photosensitizer may include at least one of the compounds represented by Chemical Formula 1.

According to an embodiment of the present disclosure, the nanoparticle may be a self-assembly of at least one of the compounds represented by Chemical Formula 1. For example, referring to FIG. 1, the nanoparticle is a self-assembly of the compound represented by Chemical Formula 1, and may be an organic photosensitizer that reacts with light irradiation (e.g., laser irradiation) to emit heat. The compound represented by Chemical Formula 1 is self-assembled in the solvent, and for example, a first solution containing a first solvent in which the compound represented by Chemical Formula 1 is dissolved is introduced into a second solvent to prepare nanoparticles through self-assembly. The first solvent is a solvent that dissolves Chemical Formula 1, and may be, for example, alcohol having 1 to 4 carbon atoms, dimethylsulfoxide (DMSO), THF, or the like. The second solvent may be a solvent having low solubility or hardly soluble in Chemical Formula 1. For example, the second solvent may be water. That is, the nanoparticles are simply synthesized through a single-step organic reaction, and are nano self-aggregates that are self-assembled in water in a simple process, which may be used as a photothermal therapeutic agent exhibiting high photothermal conversion efficiency. The nanoparticles are excellent in biocompatibility to efficiently inhibit, eliminate, reduce, and/or kill the growth of target cells (e.g., cancer or tumor cells) as a photothermal therapeutic agent.

According to one embodiment of the present disclosure, the nanoparticles may have a function of the organic photosensitizer, which may be used as an organic photothermal material for photothermal therapy.

As an example of the present disclosure, the nanoparticles may emit thermal energy by a light irradiation, and may emit heat at a temperature of 45° C. or higher in vitro or in vivo. The nanoparticles may be used as an organic photothermal material for photothermal therapy in vitro or in vivo and may emit thermal energy by a light irradiation while injected into target cells (e.g., cancer or tumor cells) or an area where the cells are distributed, and remove, kill, and/or reduce the target cells by the thermal energy. For example, the nanoparticles may have photothermal conversion efficiency of 60% or more; 70% or more; 80% or more; 90% or more; 92% or more; or 95% or more. For example, the light irradiation may be performed by using a light source in the range of an intensity of 0.5 $W/cm^2$ or more; 1 $W/cm^2$ or more; 1.25 $W/cm^2$; 1.5 $W/cm^2$; 2 $W/cm^2$ or more; or 1 $W/cm^2$ to 1.5 $W/cm^2$ and/or a wavelength of 600 nm to 1100 nm; 600 nm to 1000 nm; or 600 nm to 800 nm, for example, a laser in the red light region of 600 nm to 700 nm. Such light irradiation may be performed for 1 second or more; 1 minute or more; 2 minutes or more; 3 minutes or more; 5 minutes or more; 10 minutes or more; or 30 minutes to 1 hour. For example, the thermal energy may be emitted at 45° C. or higher; 48° C. or higher; 50° C. or higher; 60° C. or higher; or 60° C. to 70° C., and the target cells or target cell region may be heated to the temperature.

As an example of the present disclosure, the sizes of the nanoparticles may be 500 nm or less; 400 nm or less; 300 nm or less; 200 nm or less; 100 nm or less; 50 nm or less; 1 nm to 200 nm; 10 nm to 100 nm; or 20 nm to 100 nm. The size may mean a diameter, a thickness, a length, or the like according to a shape of the nanoparticle. The nanoparticles have excellent performance as a photosensitizer for photothermal therapy within the size range, and may be used as a material for photothermal therapy with easy in vivo injection and high photothermal conversion efficiency. For example, the nanoparticles may have shapes such as spheres, core cell particles, needles, nanofibers, nanotubes, and polygons.

According to an embodiment of the present disclosure, there may be provided a composition including at least one or more of the compounds represented by Chemical Formula 1 according to the present disclosure; the nanoparticles or both.

As an example of the present disclosure, the composition may emit thermal energy by a light irradiation and heat target cells to provide cell removal, killing and/or reduction functions. The composition may be used as an agent for photothermal therapy, and may remove or reduce cancer cells, tumor cells, or hyperproliferating cells in vivo or ex vivo.

As an embodiment of the present disclosure, the composition is used for the treatment of diseases, illnesses or disorders. The composition may be applied for cancer treatment of diseases, illnesses or disorders of cancer cells, tumor cells, or hyperproliferating cells, for example, solid cancer such as brain tumor, benign astrocytoma, malignant astrocytoma, pituitary adenoma, meningioma, cerebral lymphoma, oligodendroma, craniopharyngioma, ependymoma, brainstem tumor, head and neck tumor, laryngeal cancer, oropharyngeal cancer, nasal cavity cancer, nasopharynx cancer, salivary gland cancer, hypopharyngeal cancer, thyroid cancer, oral cancer, chest tumor, small cell lung cancer, non-small cell lung cancer, thymic carcinoma, mediastinal tumor, esophageal cancer, breast cancer, male breast cancer, abdominal tumor, stomach cancer, liver cancer, gallbladder cancer, biliary tract cancer, pancreatic cancer, small intestine cancer, colon cancer, anal cancer, bladder cancer, kidney cancer, male genital tumor, penile cancer, prostate cancer, female genital tumor, cervical cancer, endometrial cancer, ovarian cancer, uterine sarcoma, vaginal cancer, female external genital cancer, female urethral cancer, skin cancer, colorectal cancer, colon cancer and glioma; and blood cancer such as leukemia, malignant lymphoma, multiple myeloma or aplastic anemia, or photothermal therapy of reducing, removing and/or killing cancer cells and/or tumor cells, but is not limited thereto.

As an example of the present disclosure, the compound represented by Chemical Formula 1, the nanoparticle as a self-assembly thereof, or both may be included as pharmaceutically active ingredients. In some examples, the ingredients may be included in greater than 0% to 99%; 0.00010% to 99%; 0.0010% to 99%; 0.010% to 90%; 0.10% to 70%; 10% to 50%; 1% to 20%; or 1% to 5% (by mass) of the composition. In some examples, the ingredients may be included in concentration of $1\times10^{-5}$ M (moles) or more, preferably $1\times10^{-5}$ M (moles) to $1\times10^{-2}$ M (moles), more preferably $1\times10^{-4}$ M (moles) to $1\times10^{-2}$ M (moles). By applying the range, an appropriate photothermal effect may be provided in consideration of the size, the range, and the like of the distribution area of the target cells, and the removal and/or extinction efficiency of the target cells may be improved.

As an example of the present disclosure, the pH of the composition is 5 to 8; 6 to 8; 7 to 8 or about 7, which may be adjusted with a buffer solution.

As an example of the present disclosure, the composition further includes a carrier, and ingredients used in the technical field of the present disclosure may be applied to the carrier without deviating from the aspect of the present disclosure.

As an example of the present disclosure, the carrier includes a solvent and includes water, organic solvents, or both capable of dissolving and/or dilutes the compound represented by Chemical Formula 1 or dispersing the nanoparticles, and the solvent may be applied without limitation as long as the solvent is pharmaceutically acceptable or applicable to the composition for photothermal therapy. In some examples, the organic solvent may be alcohol having 1 to 4 carbon atoms, dimethylsulfoxide (DMSO), etc., but is not limited thereto. In some examples, the carrier may further include a pharmaceutically acceptable surfactant in order to disperse the nanoparticles. For example, the surfactant may be anionic surfactants such as sorbitan aliphatic acid ester, glycerin aliphatic acid ester, polyglycerin aliphatic acid ester, polyoxyethylene sorbitan aliphatic acid ester, etc., nonionic surfactants, natural surfactants, etc., but is not limited thereto.

According to an embodiment of the present disclosure, the composition may be applied in the form of solid (e.g., powder), gel, emulsion, suspension, liquid (e.g., injection solution), or molded product.

The present disclosure relates to a method for photothermal therapy using the compound represented by Chemical Formula 1 of the present disclosure, the nanoparticle, or both, and according to an embodiment of the present disclosure, the composition may be used and related to photothermal cancer treatment. The cancer type is as described in the composition.

According to an embodiment of the present disclosure, the method may include contacting a target cell with the compound represented by Chemical Formula 1, the nanoparticle, or both; and irradiating light to a region of the target cell contacting the compound.

As an example of the present disclosure, in the contacting of the target cells with the compound represented by Chemical Formula 1, the nanoparticle, or both, the composition may be injected or introduced into the target cell region in vitro or in vivo. The target cells may be at least one of cancer cells, tumor cells, and hyperproliferative cells. The target cells may be in vivo or ex vivo or mammalian or non-human mammalian cells.

As an example of the present disclosure, in the irradiating of the light, the light may be irradiated to the target cell region to remove, kill, and/or reduce the target cell. As an example of the present disclosure, the target cell may include the aforementioned cells. That is, thermal energy is emitted by a light irradiation, and the target cells may be removed, killed, and/or reduced by such thermal energy.

As an example of the present disclosure, in the irradiating of the light, the light irradiation may be performed by using a light source in the range of an intensity of 0.5 $W/cm^2$ or more; 1 $W/cm^2$ or more; 1.25 $W/cm^2$; 1.5 $W/cm^2$; 2 $W/cm^2$ or more; or 1 $W/cm^2$ to 1.5 $W/cm^2$ and/or a wavelength of 600 nm to 1100 nm; 600 nm to 1000 nm; or 600 nm to 800 nm, for example, a laser in the red light region of 600 nm to 700 nm. Such light irradiation may be performed for 1 second or more; 1 minute or more; 2 minutes or more; 3 minutes or more; 5 minutes or more; 10 minutes or more; or 30 minutes to 1 hour. For example, in the irradiating of the light, the temperature of the target cell region by the light irradiation may be 45° C. or higher; 48° C. or higher; 50° C. or higher; 60° C. or higher; or 60° C. to 70° C., which may remove, kill and/or reduce target cells.

According to an embodiment of the present disclosure, the method may further include analyzing a change in optical characteristics after the irradiating of the light. After the irradiating of the light, a fluorescence image of the light-irradiated cell region may be acquired or a thermal image (e.g., an infrared thermal image) of the light-irradiated cell region may be acquired to monitor the photothermal therapy process, level, and/or completion time point, etc., and control the treatment process. For the analysis, in vivo applicable analysis methods known in the art of the present disclosure may be applied, and are not specifically mentioned herein.

As follows, the present disclosure has been described with reference to the preferred embodiments of the present disclosure, but those skilled in the art will understand that the present disclosure may be variously modified and changed without departing from the spirit and the scope of the present disclosure which are defined in the appended claims.

[Scheme 1]

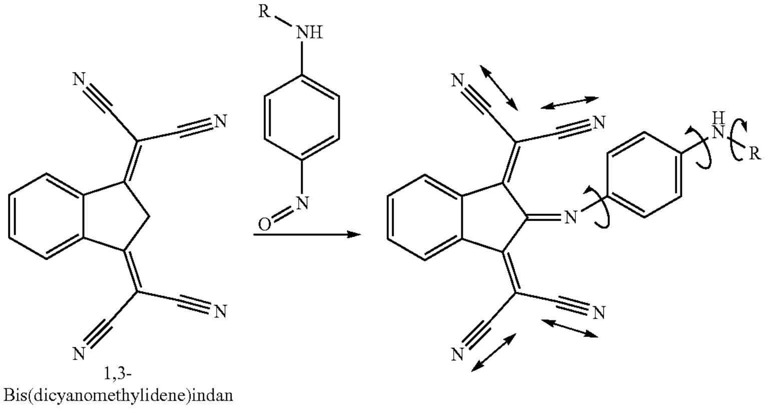

1,3-Bis(dicyanomethylidene)indan

NI1, R: 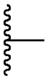

NI2, R: 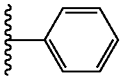

Synthesis of NI1 and NI2 Compounds

A synthesis process was performed according to Scheme 1. An indandione derivative (1.0 mml) and a nitroso compound (1.2 mmol) were dissolved in ethanol (20 mL). The mixture was refluxed for 4 hours and stored in a refrigerator overnight. The mixture was filtered and washed with cold ethanol to obtain blue powder. A product was purified by column chromatography using hexane/ethyl acetate (4/1 to 2/1 (v/v)) and then collected (yield of 50% to 90%).

NI2 was obtained without a column chromatography process. Each product may be confirmed from the results of $^{1}H$ NMR, $^{13}C$ NMR and mass spectrometry below.

Synthesis of NI3 and NI4 Compounds

[Scheme 2]

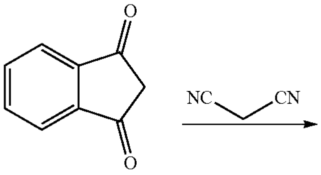

1,3-Indanedione

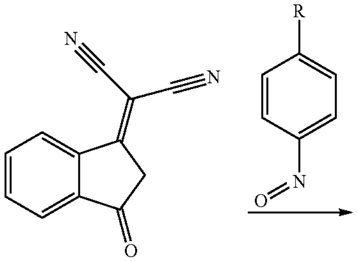

3

-continued

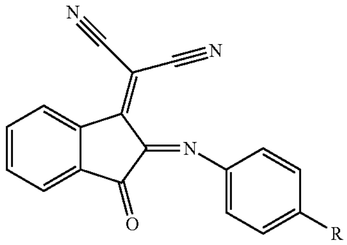

NI3

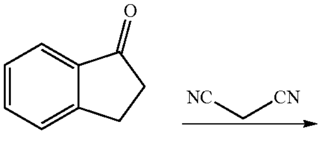

1-Indanedione

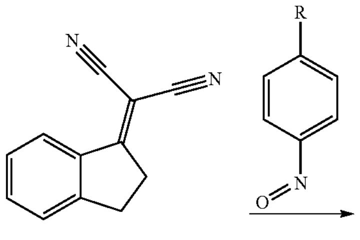

4

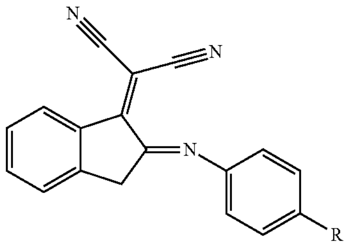

NI4

-continued a, R =

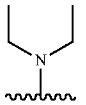

b, R =

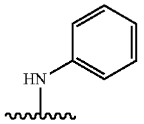

According to Scheme 2, NI3 and NI4 were synthesized by a known method. NI4b was obtained without a column chromatography process. Each product may be confirmed from the results of $^{1}H$ NMR, 13C NMR and mass spectrometry below.

NI1: $^{1}H$ NMR (400 MHz, Acetone-$d_6$) δ 8.56-8.48 (m, 2H), 8.01-7.92 (m, 2H), 7.51-7.44 (m, 2H), 6.89-6.80 (m, 2H), 3.03 (s, 3H); 13C NMR (101 MHz, ACETONE-$D_6$) δ 155.90, 154.45, 151.96, 143.33, 138.41, 137.38, 134.61, 131.37, 128.84, 128.77, 125.41, 124.70, 120.03, 114.41, 113.39, 113.18, 112.96, 73.47; ESI HRMS m/z=359.1046 $[M-H]^+$, calc. for $C_{22}H_{11}N_6$=360.11.

NI2: $^{1}H$ NMR (400 MHz, DMSO-$d_6$) δ 9.40 (s, 1H), 8.50-8.38 (m, 2H), 8.04-7.95 (m, 2H), 7.42-7.34 (m, 4H), 7.26-7.21 (m, 2H), 7.19-7.15 (m, 2H), 7.06 (tt, J=7.3, 1.2 Hz, 1H); 13C NMR (101 MHz, DMSO-$D_6$) δ 156.35, 148.05, 147.24, 141.01, 139.60, 137.45, 135.80, 130.05, 127.89, 125.96, 123.46, 120.50, 118.28, 116.41, 114.65, 113.39, 56.57; ESI HRMS m/z=423.1360 $[M+H]^+$, calc. for $C_{27}H_{15}N_6$=422.13.

NI3a: 1H NMR (400 MHz, Chloroform-d) δ 8.60 (dt, J=7.8, 0.9 Hz, 1H), 8.37-8.29 (m, 2H), 7.89-7.84 (m, 1H), 7.78-7.66 (m, 2H), 6.77-6.68 (m, 2H), 3.53 (q, J=7.2 Hz, 4H), 1.28 (t, J=7.2 Hz, 6H); 13C NMR (101 MHz, CHLOROFORM-D) δ 161.18, 159.81, 152.86, 135.28, 134.32, 125.03, 124.40, 111.95, 45.57, 12.94; ESI HRMS m/z=377.1373 $[M+Na]^+$, calc. for $C_{22}H_{18}N_4O$=354.15.

NI4a: $^{1}H$ NMR (400 MHz, Chloroform-d) δ 8.51 (d, J=8.1 Hz, 1H), 7.57 (td, J=7.5, 1.1 Hz, 1H), 7.51-7.39 (m, 4H), 6.72-6.62 (m, 2H), 3.85 (s, 2H), 3.42 (q, J=7.1 Hz, 4H), 1.19 (s, 6H); $^{13}C$ NMR (101 MHz, CHLOROFORM-D) δ 163.04, 154.10, 148.87, 145.35, 135.55, 135.22, 134.51, 128.88, 128.44, 125.89, 125.77, 115.69, 114.79, 111.77, 44.84, 36.66, 29.80, 12.78; ESI HRMS m/z=341.1759 $[M+H]^+$, calc. for $C_{22}H_{20}N_4$=340.17.

NI3b: $^{1}H$ NMR (400 MHz, Chloroform-d) δ 8.70-8.63 (m, 1H), 8.24-8.17 (m, 2H), 7.93 (d, J=7.5 Hz, 1H), 7.79 (dtd, J=26.5, 7.5, 1.2 Hz, 2H), 7.43-7.32 (m, 2H), 7.23 (d, J=1.1 Hz, 2H), 7.16 (t, J=7.4 Hz, 1H), 7.05-6.98 (m, 2H), 6.54 (s, 1H); $^{13}C$ NMR (101 MHz, CHLOROFORM-D) δ 149.64, 134.93, 133.52, 129.82, 125.41, 124.99, 124.90, 124.81, 121.98, 114.82; ESI HRMS m/z=373.1095 $[M-H]^+$, calc. for $C_{24}H_{14}N_4O$=374.12.

NI4b: $^{1}H$ NMR (400 MHz, Chloroform-d) δ 8.58-8.51 (m, 1H), 7.60 (td, J=7.5, 1.1 Hz, 1H), 7.52-7.44 (m, 2H), 7.36-7.28 (m, 4H), 7.19-7.12 (m, 2H), 7.11-7.06 (m, 2H), 7.05-7.00 (m, 1H), 6.01 (s, 1H), 3.88 (s, 2H); $^{13}C$ NMR (101 MHz, CHLOROFORM-D) δ 135.13, 129.65, 128.74, 126.71, 126.15, 125.90, 122.78, 119.67, 116.68, 36.05; ESI HRMS m/z=359.1298 $[M-H]^+$, calc. for $C_{24}H_{16}N_4$=360.14.

Preparation of Nanoparticles 1 mL of a solution of NI1 and NI2 in DMSO (2.0 mM) was slowly added dropwise to an Erlenmeyer flask containing 10 mL of air blown DW. The obtained blue solution was stored with air blowing overnight. The final NI1 NPs or NI2 NPs were collected by ultrafiltration using a 200 nm syringe filter.

Cell Culture

Mouse colon cancer CT26 cells were obtained from the Korea Cell Line Bank and the cells were cultured in a Dulbecco's modified Eagle's medium (DMEM, Corning, NY) supplemented with 10% Fetal Bovine Serum (FBS, Corning, NY) and 1% antibiotic-antifungal (Gibco, Grand Island, NY). The cells were maintained in a humidified incubator at 5% $CO_2$ and 37° C.

Cytotoxicity CT26 cells were seeded in a 96-well cell culture plate at $2\times10^4$ cells/well in a complete medium and cultured overnight to completely attach the cells to the plate. The cells were inoculated with various concentrations of NI2 NPs (0, 25, 50, 75, and 100 μM) in the complete medium and incubated for 24 hours. Next, standard 2-(4,5-dimethylthiazol-2-yl)-2,5-diphenyltetrazolium bromide (MTT) assay was performed to evaluate the cytotoxicity of NI2 NPs.

In summary, 1 mg/ml of an MTT solution was added to each well plate and kept at 37° C. for 4 hours. Next, formazan formed by adding dimethyl sulfoxide (DMSO) was further dissolved for 20 minutes. Absorbance was measured with a microplate spectrophotometer at a wavelength of 540 nm, and four independent MTT assays were performed. Based on a dosimetric test, 100 μM of NI2 NPs were used for additional in vitro and in vivo studies.

Live/Dead Cell Staining

CT26 cells were seeded in a 96-well plate at a density of $2\times10^4$ cells/well and incubated for 24 hours. Thereafter, the cells were treated with 100 μM of an NI2 NP solution and/or 691 nm laser irradiation at 1.5 W/$cm^2$ for 150 seconds to prepare four groups (CTRL, Laser, NI2 NP and Laser+NI2 NP).

Then, the treated cells were stained using both fluorescein diacetate (FDA, fluorescein diacetate) and propodeum iodide (PI). 5 mg of FDA (C7521, Sigma Aldrich, St. Louis, MO, US) was dissolved in 1 ml of acetone, and PI (P4170, Sigma Aldrich, St. Louis, MO, US) was prepared at a concentration of 2 mg/ml in PBS. Next, the FDA/PI staining solution was mixed with 5 ml of a serum-free medium, 8 μl of a FDA solution and 50 μl of a PI solution. All cells were treated with a staining solution and incubated at 37° C. for 5 minutes. Next, the cells were washed twice with PBS and observed under a fluorescence microscope (CKX53, Olympus, Tokyo, Japan). Relative intensities of green and red were measured using ImageJ (National Institute of the Health, Bethesda, MD, USA). Green and red represent viable and dead cells, respectively.

Mouse Model 16 balb/c mice (5 weeks old, female) were obtained from Hana Biotech (Suwon, Korea) for the construction of a cancer model.

All animals were maintained in an animal research facility under standard conditions. For a CT26 tumor model, a CT26 cell suspension ($1.5\times10^6$ cells/ml) was subcutaneously injected into the back of each mouse and maintained in a pathogen-free cage for one week to prepare tumors. Next, CT26 tumor-bearing mice (volume=200 $mm^3$) were randomly classified into 4 groups (N=4 per group) of CTRL, laser, NI2 NP, and laser+NI2 NP. Before the experiment, animals were anesthetized with 3% isoflurane (Terrell™ isoflurane, Piramal Critical Care, Bethlehem, PA, USA) together with oxygen (0.6 L/min). All animal studies followed the Guide for the Care and Use of Laboratory Animals of the Korea National Institute of Health (KNIH).

In Vitro Photothermal Therapy

To investigate an effect of photothermal therapy (PTT) on cancer cells, four different groups of (1) control (CTRL), (2) laser alone (Laser), NI2 NP alone (NI2 NP), (4) NI2 NP-introduced PTT (Laser+NI2 NPs) were tested. CT26 cells were previously incubated in a 96-well plate at $2\times10^4$ cells/well and placed in a humidified incubator for 24 hours. For each group, the CT26 cells were treated with either a fresh culture medium containing 100 μM NI2 NPs or a medium alone, and either irradiated with a 691 nm laser at 1.5 $W/cm^2$ for 150 seconds or not irradiated with the laser. Each test plate was incubated for 24 hours and then an MTT assay was performed to determine cell viability after each treatment.

In Vivo Photothermal Therapy

After 1 week of tumor growth, CT26 tumors were intratumorally injected with saline or 100 μM NI2 NPs and exposed to a 691 nm laser (1.5 $W/cm^2$ for 150 seconds) under anesthesia. An IR thermal imaging camera was used to monitor a temperature change of a tumor region during laser irradiation. A single treatment was applied to all animals and a beam size of optical fiber was adjusted to cover the entire tumor area. Thereafter, all mouse groups were monitored and pictures were measured by using a digital camera (D5100, Nikon, Tokyo, Japan) was taken at four time points of day 0 (DO), day 3 (D3), day 7 (D7), and day 10 (D 10) after each treatment. The tumor volume of each group was measured for 10 days using Formula (tumor volume=length×width$^2$).

Table 1 shows photophysical and photothermal characteristics of NI1 to NI4. absorption wavelength in $^{\alpha}$DMSO; molar absorption coefficient ε; energy gap $E_g$ between HOMO and LUMO levels; photothermal conversion efficiency η(%).

TABLE 1

| | $\lambda_{abs}^{\alpha}$ (nm) | ε ($\times10^3$) | $E_g$ (eV) | η (THF) | η (DMSO) | η (NPs) |
|---|---|---|---|---|---|---|
| NI1 | 728 | 12.0 | 2.23 | 31.4 | 50.3 | 58.3 |
| NI2 | 690 | 15.6 | 2.10 | 32.4 | 52.1 | 92.5 |
| NI3a | 624 | 28.9 | 2.57 | — | — | 11.6 |
| NI3b | 619 | 32.3 | 2.52 | — | — | 46.4 |
| NI4a | 596 | 16.8 | 2.56 | — | — | 7.24 |
| NI4b | 568 | 20.1 | 2.54 | — | — | 29.6 |

[Mechanism 1]

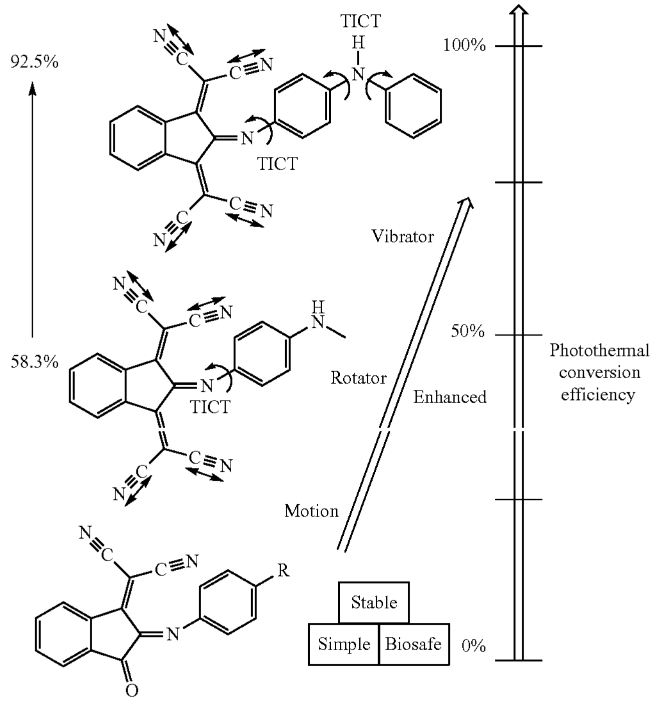

[Jablonski diagram]

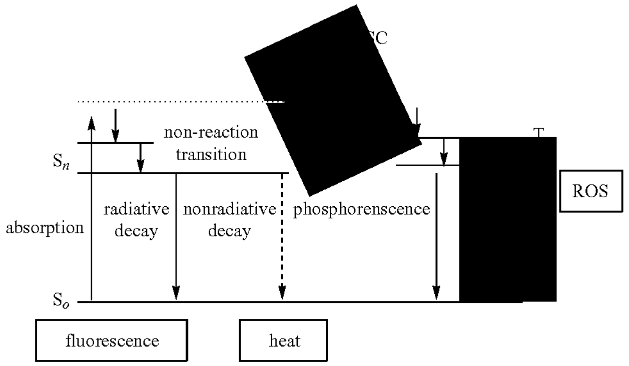

Referring to Table 1, the mechanism and the Jablonski diagram related to three types of energy dissipation of an excited fluorophore, the N12 compound according to the present disclosure exhibits high photothermal conversion efficiency (η) of 92.5%, and the large photothermal effect is due to (1) radiative decay by an intersystem crossing (ISC) process and non-radiative decay derived from twisted C═N bonds in which fluorescence emission through generation of reactive oxygen species (ROS) is completely suppressed. In addition, the photothermal effect may be improved by (2) synergistic twisted intramolecular charge transfer (TICT) effect, a strong D-A force, various intramolecular vibrators and rotators. The formation of J-aggregated NPs may enhance an intramolecular D-A structure by π-π interactions and stacking, which induces extended 7n-conjugation.

Moreover, as illustrated in FIG. 1, the nano-aggregates obtained by self-assembling the N12 compound in water by a simple method may efficiently inhibit tumor growth after 10 days of PTT treatment with excellent biocompatibility in a mouse tumor model.

Figure 2:
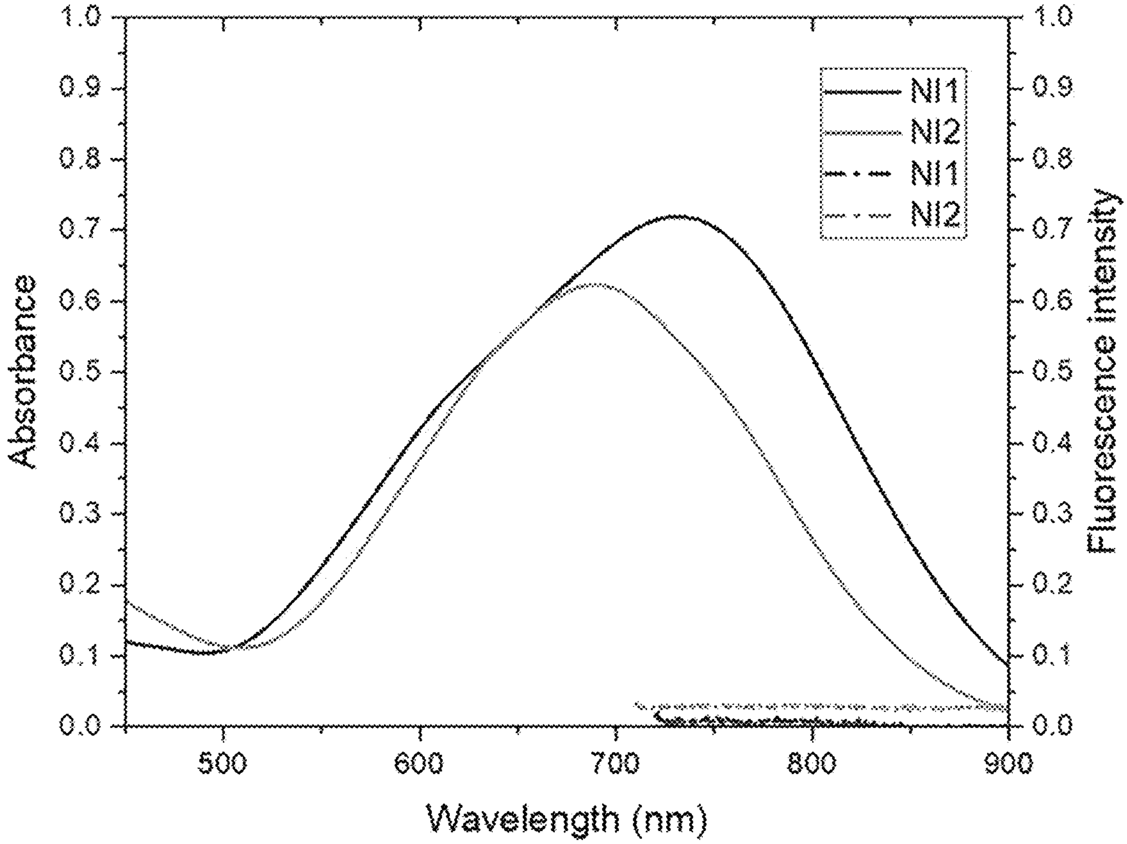
FIG. 2 illustrates UV-Vis absorption (solid line) and fluorescence emission (dotted line) spectra of NI1 (60 μM) and NI2 (40 μM) in DMSO according to an embodiment of the present disclosure.

In the UV-Vis spectrum of FIG. 2 and Table 1, an absorption peak of NI1 has a tendency of red-shift absorption ($\lambda_{abs}$=728 nm, in DMSO) compared to NI2 ($\lambda_{abs}$=690 nm, in DMSO) in an organic solvent. In addition, the NI1 has the absorption at about 690 nm in 40 μM of an NI2 solution (in DMSO), but does not show fluorescence. The molar absorption coefficient (8) of NI1 is relatively lower than that of NI2, which generates a conjugate in a free pair of electrons of an —NH group due to the introduction of a phenyl group in NI2 and may reduce an ICT effect from an electron donor group to an electron acceptor group compared to NI1.

Figure 3A:
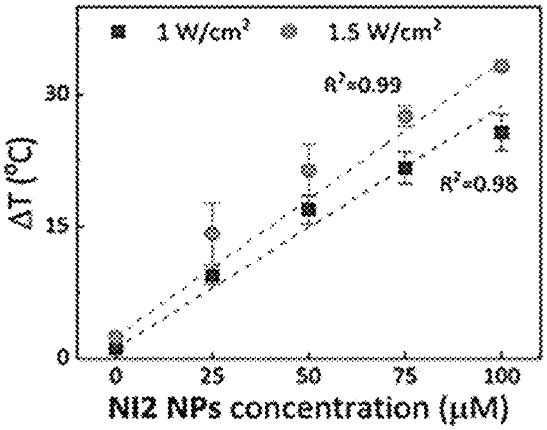
FIGS. 3A, 3B, and 3C relate to the thermal reaction of NI2 NPs according to 691 nm laser irradiation at 1 $W/cm^2$ and 1.5 $W/cm^2$ according to an embodiment of the present disclosure.
Figure 3B:
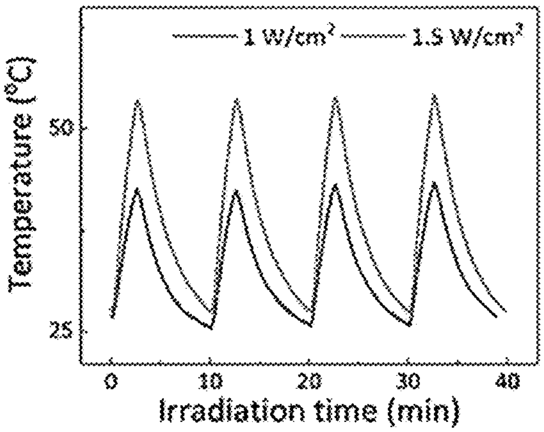
Figure 3C:
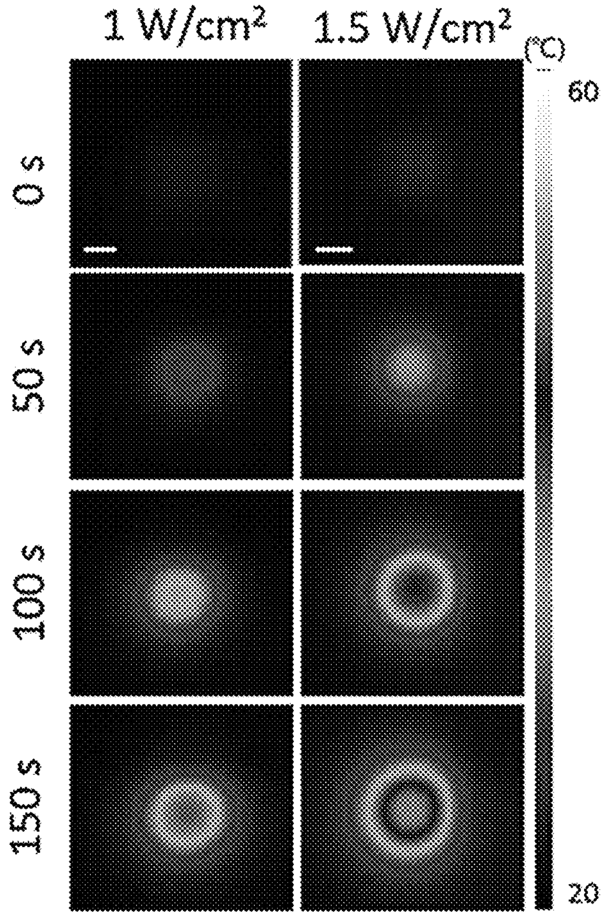

FIGS. 3A, 3B and 3C show quantitative analysis results of the photothermal characteristics and photothermal conversion efficiency of NI2 nanoparticles according to various concentrations and laser irradiation times in a 691 nm laser (1 W/cm$^2$ and 1.5 W/cm$^2$) irradiation of NI2 nanoparticles. When the concentration of the NI2 solution (in D.W.) was changed from 0 to 100 μM, it could be seen that the temperature increased in proportion to the concentration when the temperature change of the NI2 solution was measured after absorption for 150 seconds. That is, in FIG. 3A, it may be seen that a temperature increase (ΔT) changes linearly after irradiation for 150 seconds ($R^2$=0.98 to 0.99), and the maximum temperature of the NI2 NP was 42.8±2.8° C. and 54.4±0.5° C. for 1 W/cm$^2$ and 1.5 W/cm$^2$ at 100 μM, respectively. In FIG. 3B, photothermal stability may be confirmed in 4 cycles under 691 nm irradiation. In FIG. 3C, it may be seen in the captured sequential thermal images showing the "spatio-temporal distribution" in the temperature area.

Figure 4A:
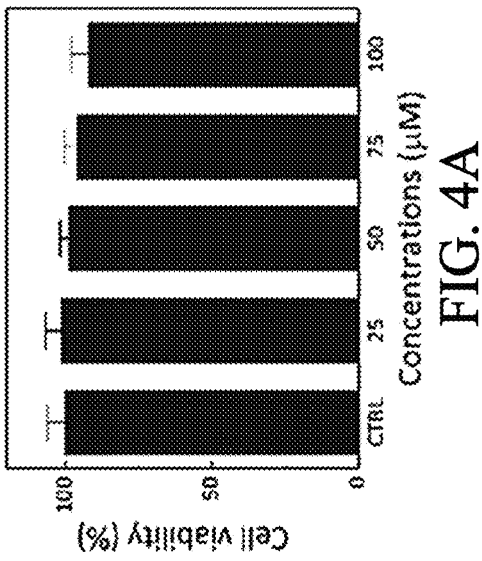
FIGS. 4A, 4B, 4C, 4D, and 4E relate to in vitro characterization of NI2 NPs under various conditions according to an embodiment of the present disclosure.
Figure 4B:
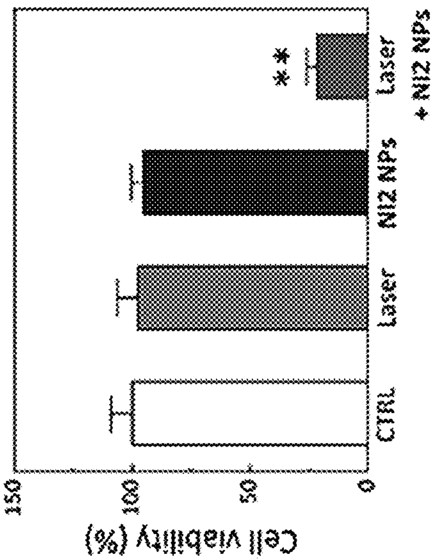

In FIGS. 4A, 4B, 4C, 4D, and 4E, there is no change in cancer cells when CTRL having a very small temperature change is injected into cancer cells CT26, and there is no change in cancer cells when laser light is irradiated on cancer cells CT26. In FIGS. 4A, 4B, 4C, 4D, and 4E, as a result of an in vitro test of an NI2-NP organic photothermal cancer therapy agent, it may be seen that cancer cells are reduced when cancer cells CT26 are irradiated with laser light and injected with NI2-NP. That is, in FIG. 4A, the cytotoxicity of NI2 NP in CT26 rat cancer cells was tested as a function of concentration using a standard MTT assay. After incubation for 24 hours, NI2 NPs show no significant cytotoxicity in CT26 cells even at the highest concentration of 100 μM without laser irradiation and has cell viability of 90% or more to have excellent biocompatibility at the cellular level, so that 100 μM was selected as the maximum NI2 NP concentration for further in vitro and in vivo testing. In FIG. 4B, it may be seen that the cell viability decreases in "Laser+NI2 NPs" (p<0.005 vs. CTRL).

Figure 4C:
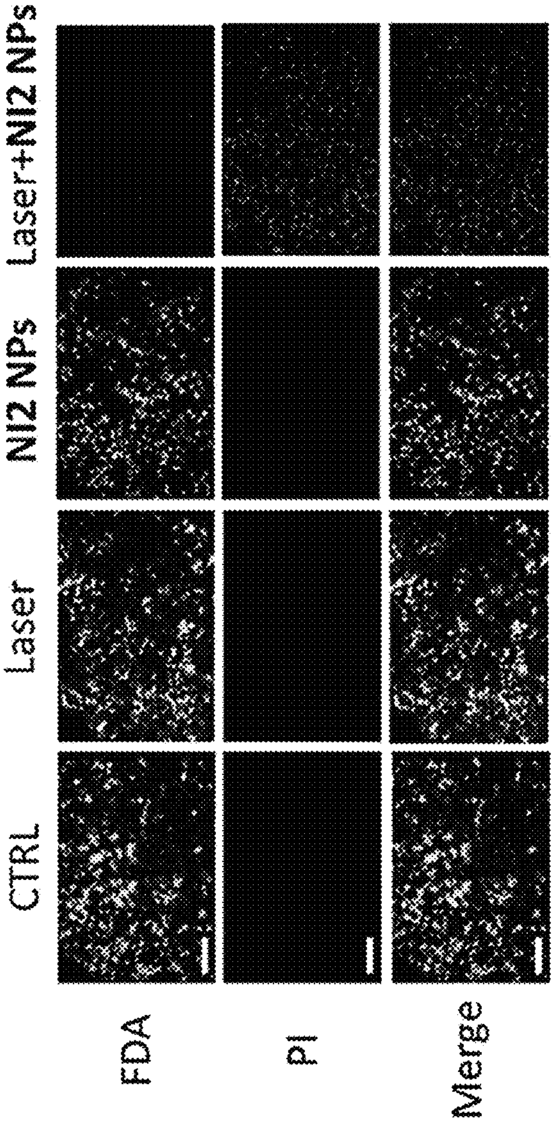
Figure 4D:
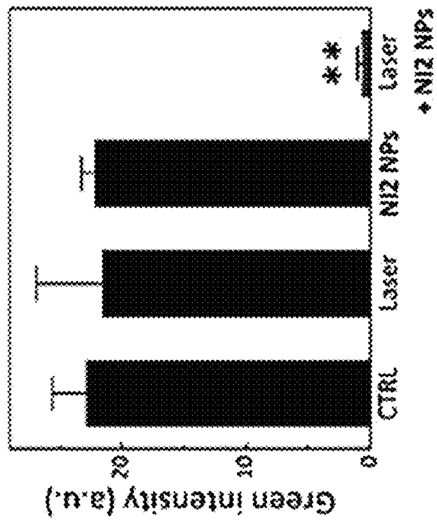
Figure 4E:
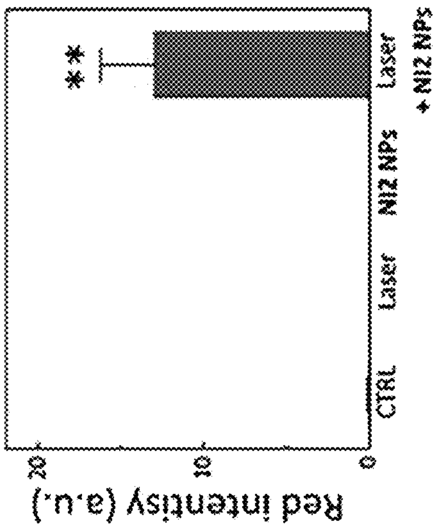

"Laser+NI2 NPs" shows bright red fluorescence (stained with PI), indicating non-viable cells after combined treatment, and the green and red intensities measured in FIG. 4C confirmed the unique anti-tumor effect of NI2 NP-assisted PTT on CT26 cells (FIGS. 4D and 4E, p<0.05 vs. CTRL).

In FIGS. 5A and 5B, and 6A, 6B, 6C, and 6D, when CTRL, which gives a very small temperature change, is injected into cancer cell CT26 present in mice, there is no change in cancer cells in thermal imaging. When irradiating laser light on cancer cells CT26 present in mice, there is no change in cancer cells in thermal imaging. The laser light irradiation and NI2 NP injection in mice reduced cancer cells in thermal imaging (see: in vivo test of NI2-NP for organic photothermal cancer therapy agent).

Figure 5B:
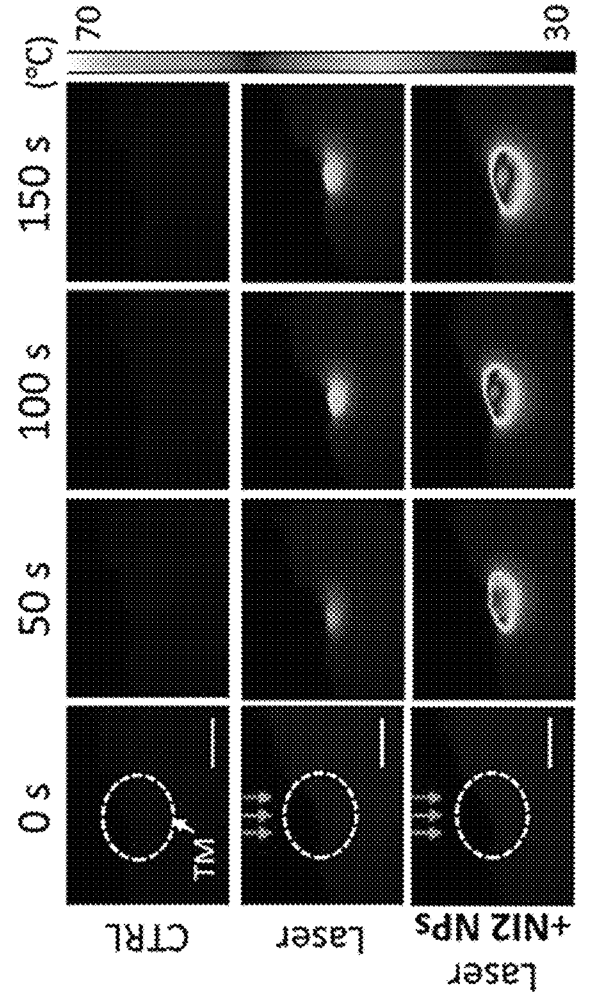
FIGS. 5A and 5B illustrate in vivo thermal imaging evaluation of NI2NP-applied photothermal therapy (100 μM and 1.5 $W/cm^2$ for 150 s) in a CT26 tumor-bearing model, according to an embodiment of the present disclosure.
Figure 5A:
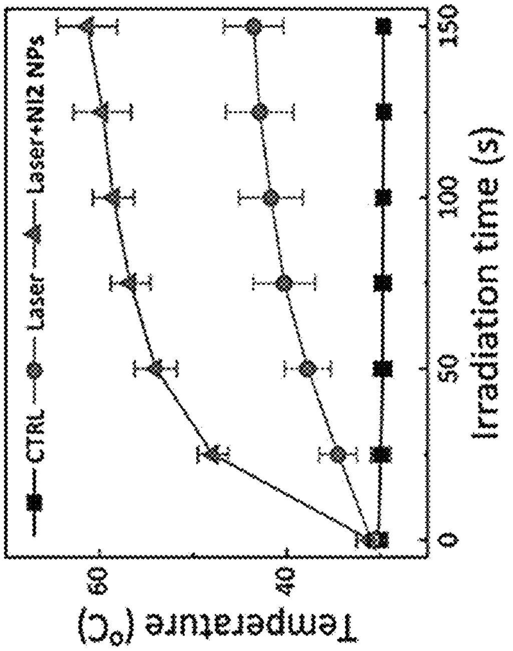

That is, FIGS. 5A and 5B illustrate assays for photothermal efficiency with a CT26 tumor-bearing mouse model of NI2 NP, and under different treatment conditions (CTRL, Laser, and Laser+NI2 NPs (100 μM of NI2 NPs and 1.5 W/cm$^2$/150 s), NI2 NPs were intratumorally administered to each animal before laser irradiation. 691 nm laser light was transmitted through an optical fiber perpendicularly to the tumor site with and without NI2 NP injection. In the case of Laser and Laser+NI2 NPs, the surface temperature of the tumor initially increased with an irradiation time, but became saturated at around 40° C. and 60° C., respectively (FIG. 5A). Laser+NI2 NPs has a maximum temperature (maximum 61.3±3.2° C.) that is 1.5 times higher than that of Laser, which exceeded a threshold for irreversible tumor necrosis. Although a Laser group increased a tumor temperature due to the inherent absorption of light by the skin tissue and blood, the maximum temperature is not sufficient to cause irreversible damage to the entire tumor, and CTRL shows a negligible temperature change. FIG. 5B shows sequential thermal images of tumors according to various treatment times in three conditions, and both Laser and Laser+NI2 NPs show a noticeable temperature increase at the tumor surface with a Gaussian profile of a temperature field. At the end of irradiation (150 seconds), it was confirmed that Laser+NI2 NPs generate a maximum temperature (61.3° C.) higher than Laser (43.5° C.), and both "CTRL" and "NI2 NP" did not induce the temperature change at the tumor site (data not shown).

Figure 6A:
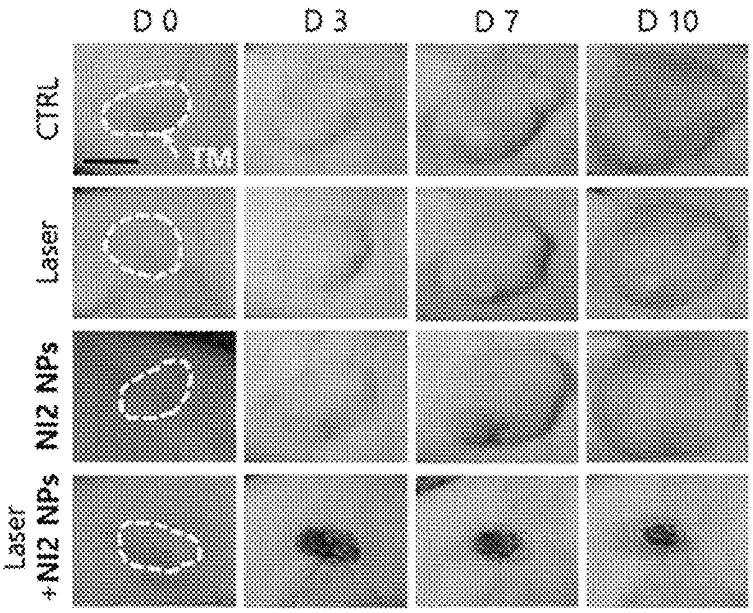
FIGS. 6A, 6B, 6C, and 6D illustrate in vivo antitumor effects of NI2 NP adjuvant photothermal therapy (100 μM and 1.5 W/$cm^2$ for 150 s) on a CT26 tumor bearing model according to an embodiment of the present disclosure.
Figure 6B:
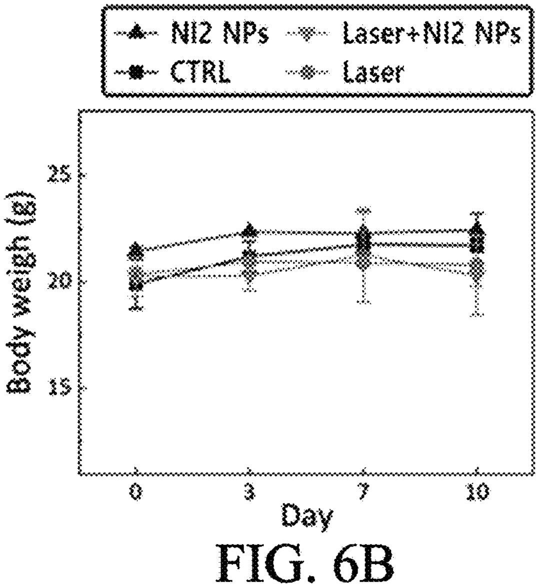

FIGS. 6A, 6B, 6C, and 6D show results after experiments of an in vivo model at 4 different day points (DO, D3, D7 and D10) under 4 different treatment conditions (CTRL, Laser, and Laser+NI2 NPs). In a plan view of the treated tumors in FIG. 6A, the CTRL, Laser, and NI2 NPs groups included obvious tumor growth after each treatment. On the other hand, the Laser+NI2 NPs group may show clear tumor resection with wound healing. All groups show no significant weight loss for 10 days after treatment (FIG. 6B).

Figure 6C:
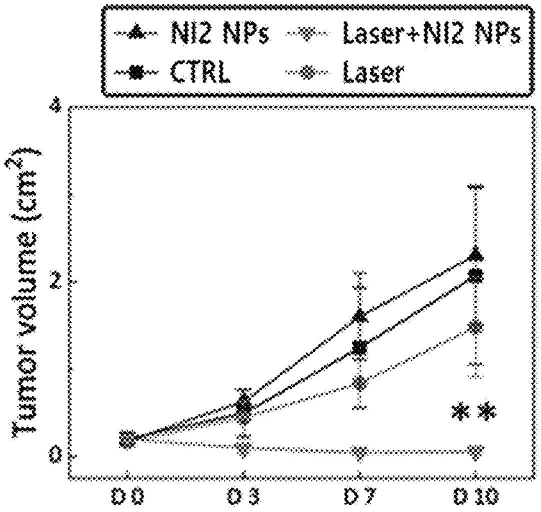

According to FIG. 6C, CTRL, laser, and NI2 NPs have negligible therapeutic efficacy with a significant increase in tumor volume over time, but Laser+NI2 NPs may confirm complete tumor removal (p<0.005 compared to other groups at D10).

Figure 6D:
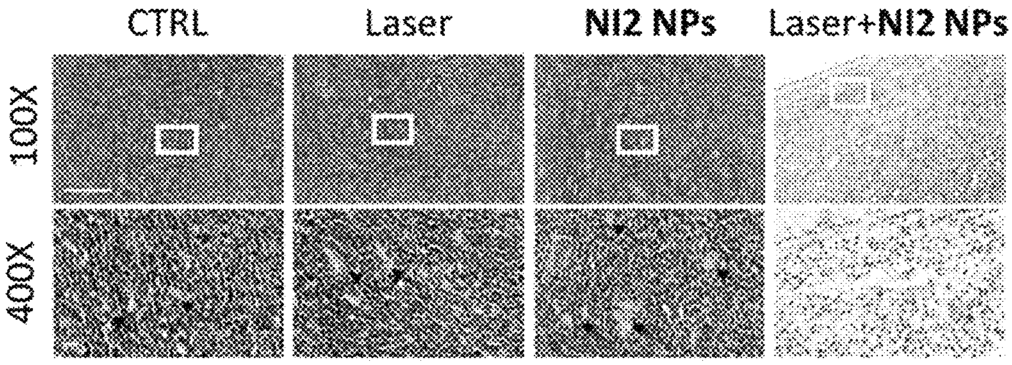

In FIG. 6D, histological examination was performed on all samples treated to evaluate the efficacy of NI2 NP-assisted PTT at D10. Samples treated with Laser+NI2 NPs may show unique tissue damage without capillaries found in the tumor site. Conversely, other treatment groups maintain the intrinsic morphology and nuclear structure of the tumor tissue. Due to excessive proliferation of tumor cells after incomplete treatment, many tumor cells and capillaries are densely distributed in the tumor site.

According to the present disclosure, D-A structured NI1 and NI2 were synthesized by one step reaction, and particularly, an amino-phenyl group serves as an electron-donating moiety and a molecular rotor for twist to acquire a specific conformation, whereas 1,3-bis(dicyanomethylidene)indan may serve as an electron-acceptor moiety and a potent contributor of intramolecular stretching vibration to maintain a certain intramolecular motion. These twisted structures NI1 and NI2 with strong D-A force and various intramolecular oscillators and rotors show the fluorescence emission due to C═N bonds and the unsettling of the ISC process, and this could be a potential candidate for thermal deactivation through non-radiative energy dissipations. NI1 and NI2 nanoaggregates (NI1 NP and NI2 NP) exhibit excellent photothermal conversion efficiency (η) of 58.3% and 92.5%, respectively. In an in vivo experiment, NI2 NPs may provide significant effects in thermal imaging and photothermal therapy of tumors.

In the present disclosure, NI2-NP shows excellent photothermal conversion efficiency (e.g., 90% or more) compared to many small organic photothermal agents by overcoming disadvantages of some existing small organic photothermal agents (e.g., low photostability of cyanide derivatives, low water solubility of porphyrin and phthalocyanine, low photothermal conversion efficiency of BODIPY derivatives, etc.). As a result of in vivo experiments, NI2-NP may provide remarkably effective results for thermal imaging and photothermal treatment of tumors.

According to the present disclosure, it is possible to provide an organic photosensitizer capable of being produced by a simple synthesis method and having high photothermal conversion efficiency, and the organic photosensitizer may conveniently perform commercialization, biological applications, and clinical trials. That is, it is possible to have excellent photothermal conversion efficiency in addition to the advantages of a small organic photothermal agent recognized as an excellent photothermal therapeutic agent, and to be synthesized through a simple single-step organic synthesis to conveniently perform commercialization, biological applications, and clinical trials. In addition, as a photothermal therapeutic agent with excellent biostability and biocompatibility, it is possible to contribute to a design of additional molecules for multimodal photoacoustic and induced photothermal cancer therapy and promote commercial and clinical applications of small organic photothermal diagnostic agents.

As described above, although the embodiments have been described by the restricted embodiments and the drawings, various modifications and variations may be made from the above description by those skilled in the art. For example, even if the described techniques are performed in a different order from the described method, and/or components such as a system, a structure, a device, a circuit, etc. described above are coupled or combined in a different form from the described method, or replaced or substituted by other components or equivalents, an appropriate result may be achieved. Therefore, other implementations, other embodiments, and equivalents to the appended claims fall within the scope of the claims to be described below.

What is claimed is:

1. A compound represented by Chemical Formula 1:

[Chemical Formula 1]

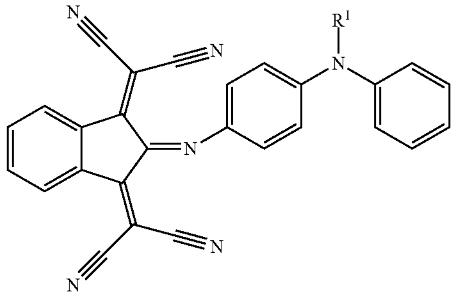

wherein $R^1$ is selected from a substituted or unsubstituted cycloalkyl group having 3 to 6 carbon atoms, a substituted or unsubstituted cycloalkenyl group having 3 to 6 carbon atoms, a substituted or unsubstituted aryl group having 6 to 12 carbon atoms, a substituted or unsubstituted heteroaryl group having 5 to 12 carbon atoms, an alkyl group having 1 to 10 carbon atoms, an alkenyl group having 2 to 10 carbon atoms, and an alkynyl group having 2 to 10 carbon atoms; and wherein when $R^1$ is selected from a substituted cycloalkyl group having 3 to 6 carbon atoms, a substituted cycloalkenyl group having 3 to 6 carbon atoms, a substituted aryl group having 6 to 12 carbon atoms, and a substituted heteroaryl group having 5 to 12 carbon atoms, the substitution is selected from one of an alkyl having 1 to 5 carbon atoms, alkenyl having 2 to 5 carbon atoms, alkynyl having 2 to 5 carbon atoms, and a halogen atom.

2. The compound of claim 1, wherein the compound is provided in the form of an aggregate nanoparticle.

3. The compound of claim 2, wherein the nanoparticle has a size of 500 nm or less, and the nanoparticle emits heat at a temperature of 45° C. or higher by a light irradiation.

4. The compound of claim 2, wherein a photothermal conversion efficiency of the nanoparticle is 60% or higher.

5. A composition comprising:

the compound represented by Chemical Formula 1 of claim 1.

6. The composition of claim 5, wherein the composition is used for photothermal therapy, and emits thermal energy during a light irradiation to remove or kill target cells.

7. The composition of claim 6, wherein the target cells comprise cancer cells, tumor cells or hyperproliferative cells.

8. The composition of claim 5, further comprising:

water, an organic solvent, or both, wherein the compound in the composition is included in an active ingredient content.

9. A method for photothermal therapy, the method comprising:

contacting the composition of claim 5 with a target cell in vivo or ex vivo; and irradiating light to a region of the target cell contacting the composition.

10. The method of claim 9, wherein the irradiating of the light comprises heating a target cell region to a temperature of 45° C. or more by irradiating a red light laser of 1 second or more and 1 $W/cm^2$ or more and removing or killing the target cell.

11. The method of claim 9, further comprising:

after the irradiating of the light, acquiring and analyzing an infrared thermal image of the target cell region.

* * * * *